United States Patent [19]

Wilmes et al.

[11] Patent Number: 5,744,633
[45] Date of Patent: Apr. 28, 1998

[54] PROCESS FOR THE PRODUCTION OF DIURETHANES AND THEIR USE FOR THE PRODUCTION OF DIISOCYANATES

[75] Inventors: Oswald Wilmes, Köln; Eberhard König, Leverkusen; Klaus Nachtkamp, Düsseldorf; Ernst Kysela, Bergisch Gladbach, all of Germany

[73] Assignee: Bayer Aktiengesellschaft, Leverkusen, Germany

[21] Appl. No.: 348,704

[22] Filed: Dec. 2, 1994

[30] Foreign Application Priority Data

Dec. 13, 1993 [DE] Germany ............... 43 42 426.0

[51] Int. Cl.$^6$ ............................................. C07C 261/00
[52] U.S. Cl. ................................. 560/115; 560/158
[58] Field of Search ............................. 560/158, 115

[56] References Cited

U.S. PATENT DOCUMENTS

| | | | |
|---|---|---|---|
| 2,409,712 | 10/1946 | Schweitzer | 260/453 |
| 2,806,051 | 9/1957 | Brockway | 260/471 |
| 4,388,238 | 6/1983 | Heitkämper et al. | 260/239 E |
| 4,388,246 | 6/1983 | Sundermann et al. | 260/453 P |
| 4,430,505 | 2/1984 | Heitkamper | 560/158 |
| 4,497,963 | 2/1985 | Merger | 560/158 |
| 4,596,678 | 6/1986 | Merger et al. | 560/344 CM |
| 4,596,679 | 6/1986 | Hellbach et al. | 560/344 |
| 4,611,079 | 9/1986 | Merger et al. | 560/25 |
| 4,692,550 | 9/1987 | Engbert et al. | 560/345 |
| 4,713,476 | 12/1987 | Merger et al. | 560/115 |
| 4,851,565 | 7/1989 | Merger et al. | 560/115 |
| 5,087,739 | 2/1992 | Bohmholdt et al. | 560/345 |
| 5,284,969 | 2/1994 | Hauner et al. | 560/345 |

FOREIGN PATENT DOCUMENTS

| | | |
|---|---|---|
| 1144562 | 4/1983 | Canada . |
| 2094484 | 10/1993 | Canada . |
| 2095417 | 11/1993 | Canada . |
| 4-164060 | 6/1992 | Japan . |
| 982785 | 2/1965 | United Kingdom . |

OTHER PUBLICATIONS

ADAMS, Chemical Reviews, vol. 65, pp. 567–602, 1965.
Ault, "Techniques and Experiments for Organic Chemistry," 4th Ed., pp. 304–306, 1983.

*Primary Examiner*—Michael L. Shippen
*Attorney, Agent, or Firm*—Joseph C. Gil; Lyndanne M. Whalen

[57] ABSTRACT

A new process for the production of high purity (cyclo) aliphatic diurethanes from (cyclo)aliphatic diamines, alcohols and urea in a multistep reaction in which (1) urea is reacted with alcohol with elimination of ammonia, (2) diamine is then introduced into the reaction mixture, optionally in the form of a solution in alcohol, and reacted with continuous release of ammonia and (3) the reaction mixture is freed from volatile components by distillation. The diurethanes produced by this process are useful as starting materials for the production of the corresponding diisocyanates by thermal urethane cleavage.

6 Claims, No Drawings

PROCESS FOR THE PRODUCTION OF DIURETHANES AND THEIR USE FOR THE PRODUCTION OF DIISOCYANATES

BACKGROUND OF THE INVENTION

This invention relates to a process for the production of high-purity (cyclo)aliphatic diurethanes from (cyclo)aliphatic diamines, urea and alcohols with release of ammonia and to the use of these diurethanes for the production of (cyclo)aliphatic diisocyanates by thermal urethane cleavage.

The urethanization of (cyclo)aliphatic amines with urea or carbamic acid esters and alcohols is known in principle. EP-A-0 018 586 discloses that (cyclo)aliphatic diurethanes based on lower (cyclo)aliphatic alcohols (boiling point of the alcohol<180° C.) are obtained in yields of more than 90% but does not disclose anything with respect to the purity of these diurethanes. Where high-boiling alcohols (boiling point of the alcohol >180° C.) are used, it can be seen from the Examples that secondary products are present in some cases in considerable quantities (up to 25%).

According to Applicants' own experience, oligoureas and polyureas are also formed where low-boiling alcohols are used in the process described in EP-A-0 018 586. Oligoureas and polyureas can seriously interfere with thermal urethane cleavage. A single recrystallization would not be expected to completely remove the oligoureas and polyureas. The oligoureas and polyureas would therefore contaminate the product. As a result, the actual yields obtained in the Examples of EP-A-0 018 586 are probably lower than the stated yields. In addition, Applicants' own recrystallization tests have shown that the oligoureas and polyureas present as impurities are actually enriched by the purifying operation described in the Examples of EP-A-0 018 586. EP-A-0 018 588 discloses a process in which N-unsubstituted carbamic acid esters instead of urea are used as the "carbonyl source" in its Examples. No purities are disclosed for the products made using low-boiling alcohols (boiling point of the alcohol<180° C.) and the yields obtained are below those reported in EP-A-0 018 586. It may therefore be assumed that the content of secondary products in the products obtained in EP-A-0 018 588 is actually increased.

The use of catalysts to increase the reaction rate is recommended both in EP-A-0 018 586 and in EP-A-0 018 588. The disadvantage of following this recommendation is that some of the catalyst may remain in the product. Each of these disclosures teaches that it may be useful, particularly in the reaction of low molecular weight alcohols under pressure, to remove the ammonia generated during the reaction by means of a stripping agent which is inert under the reaction conditions (for example, a gas such as nitrogen). However, this procedure has the disadvantage that, when it is applied on an industrial scale, an additional waste gas treatment step must be included. Such a step is particularly expensive.

Other processes for the production of diurethanes from the corresponding diamines, alcohols and low molecular weight "carbonyl sources" are described, for example, in EP-A-0 027 940, EP-A-0 027 952, EP-A-0 027 953, EP-A-0 126 299, EP-A-0 126 300, EP-A-0 355 443, EP-A-0 566 925 or DE-OS 4 231 417.

The Examples given in these prior publications generally contain no data with respect to the purity of the diurethanes obtained. However, Applicants' own studies have shown that the diurethanes obtained by these known processes cannot be cleaved without at least partially removing the oligoureas and polyureas formed as secondary products in a preliminary treatment. If the oligoureas and polyureas are not at least partially removed, considerable loss of yield and unfavorable side effects (for example, resin-like deposits in the cleavage reactor) occur.

SUMMARY OF THE INVENTION

The problem addressed by thee present invention was to provide a process for the production of high-purity (cyclo)aliphatic diurethanes which would be particularly suitable for the production of (cyclo)aliphatic diisocyanates by thermal urethane cleavage. Secondary products which might accumulate in small quantities should be easy to remove and recycle.

Surprisingly, this problem is solved by (1) reacting urea with alcohol and removing ammonia, (2) subsequently reacting a diamine (optionally in dissolved form) with the mixture from (1) without intermediate isolation while ammonia is continuously released. The diurethane is obtained in pure form by distillation to remove excess alcohol and urea derivatives which are volatile in vacuo at elevated temperature.

DETAILED DESCRIPTION OF THE INVENTION

The present invention relates to a process for the production of diurethanes corresponding to Formula (I):

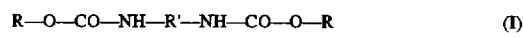

R—O—CO—NH—R'—NH—CO—O—R   (I)

in which diamines corresponding to formula (II):

H$_2$N—R'NH$_2$   (II)

are reacted with the reaction product of urea and an alcohol corresponding to formula (III):

R—OH   (III)

in which

R represents the residue obtained by removal of the hydroxyl group from a monohydric alcohol which alcohol has a boiling point at normal pressure below 180° C. and R' represents a difunctional (cyclo)aliphatic hydrocarbon radical containing from 2 to 18 (preferably 4 to 15) carbon atoms, with the proviso that at least 2 carbon atoms are arranged between the two nitrogen atoms.

In the first stage of this process, urea is reacted with the monohydric alcohol corresponding to formula (III) in an amount such that the molar ratio of alcohol to urea is at least 1:1 at a temperature of from about 150° to about 300° C. with elimination and removal from the reaction mixture of at least 10 mol % of ammonia, based on the molar quantity of urea used. In a second stage, the diamine corresponding to formula (II), optionally dissolved in an alcohol corresponding to formula (III), is introduced into the reaction mixture from the first stage and reacted at a temperature of from about 150 to about 300° C. with continuous release of ammonia. In a third stage, the reaction mixture is freed from volatile constituents by distillation.

The present invention also relates to the use of the diurethanes obtainable by this process as starting materials in processes for the production of the corresponding diisocyanates by thermal urethane cleavage.

Starting materials for the process of the present invention are diamines corresponding to formula (II), urea and alcohols corresponding to formula (III).

Suitable diamines corresponding to formula (II) include: butane1,4-diamine, 1-methylpentane-1,5-diamine, 2-methylpentane-1,5-diamine, hexane-1,6-diamine, 2,2,4- and 2,4,4-trimethylhexane-1,6-diamine, cyclohexane-1,3-diamine, cyclohexane-1,4-diamine, 2-methyl- and/or 4-methylcyclohexane-1,3-diamine (hydrogenated tolylenediamine), 1,3- and 1,4-diaminomethyl cyclohexane, bis-(4-aminocyclohexyl)-methane, bis-(4amino-3-methyl cyclohexyl)-methane, 3-aminomethyl-3,5,5-trimethyl cyclohexylamine (isophoronediamine) and 3- and/or 4-aminomethyl-1-methyl cyclohexylamine.

Particularly preferred diamines corresponding to formula (II) are hexane-1,6-diamine (HDA), 3-aminomethyl-3,5,5-trimethyl cyclohexylamine (IPDA) and bis-(4-aminocyclohexyl)-methane.

Suitable alcohols corresponding to formula (III) include any of the aliphatic or cycloaliphatic alcohols having a boiling point at normal pressure below 180° C. Examples of such alcohols include: $C_{1-6}$ alkanols such as methanol, ethanol, n-propanol, n-butanol or n-hexanol and cyclohexanol. A particularly preferred alcohol is n-butanol.

In the process of the present invention, the urea serving as carbonyl source is first reacted with the alcohol corresponding to formula (III). Ammonia is released during this reaction. This reaction is carried out at a temperature of from about 150° to about 300° C., preferably from about 160° to about 250° C. An at least equimolar quantity, preferably 1.2 to 25 times, and more preferably 1.2 to 10 times the molar quantity of alcohol, based on urea, is generally used. The reaction is carried out until at least 10 mol %, preferably from about 30 to about 90 mol % of ammonia, based on the molar quantity of urea used, has escaped from the reaction mixture. It may be assumed that at least 10%, preferably from about 30 to about 90% of the ammonia theoretically expected in the event of complete reaction of the urea and the N-unsubstituted carbamate in accordance with the following equation:

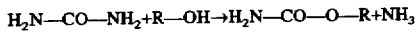

is eliminated. A pressure reactor equipped with a stirrer, reflux condenser and pressure-holding valve may be used to carry out this reaction. The pressure-holding valve may be adjusted in such a way that excess alcohol boils under reflux and ammonia can escape in gaseous form.

In the second stage of the process of the present invention, the diamine corresponding to formula (II) is added either in pure form, optionally as a melt, or preferably in the form of an at least 5% by weight solution in a further quantity of alcohol corresponding to formula (III). The diamine is added to the reaction mixture gradually at a temperature in the range of from about 150° to about 300° C., preferably at a temperature of from about 160° to about 250° C., again with release of ammonia. The pressure in the reactor is preferably adjusted in such a way that the alcohol present in excess boils under reflux.

The quantity of the diamine is generally such that from about 0.1 to about 0.5 mol, preferably from about 0.3 to about 0.5 mol of diamine is used for every mol of urea used in the first stage of the process. The total quantity of alcohol used in both the first and second stages will generally be between 1 and 25 mol, preferably between 1.2 and 10 mol, per mol of urea used in the first stage of the process.

In general, the reaction mixture is stirred under the reaction conditions mentioned until the release of ammonia abates (after about 1 to 2 hours). The reaction mixture is then stirred for a certain time (for example, at least one hour) under the described reaction conditions and, is then delivered to the third stage where it is worked up by distillation.

In this distillation-based working-up stage, the low-boiling fraction (excess alcohol) is first removed by distillation after which medium-boiling constituents present in quantities of at most 20% by weight, based on the diurethane formed, are removed by distillation, for example in a vacuum of 0.001 to 500 mbar. Medium-boiling fractions are believed to be (i) the N-unsubstituted carbamic acid ester corresponding to the alcohol, (ii) N,O-disubstituted carbamic acid ester of which the substituents correspond to the alcohol used and (iii) the di(cyclo)alkyl carbonates corresponding to the alcohol used.

After working up by distillation in this stage, the diurethanes are obtained in a purity of approximately 99%. The only significant secondary product remaining is the urea derivative corresponding to the alcohol used. This secondary product corresponds to the formula:

and may be isolated by preparative gel-permeation chromatography and identified by NMR spectroscopy. If desired, the end product of the process may also be freed from the small quantities of this secondary product by high-vacuum distillation. However, this is generally not necessary in view of the low concentration of this "impurity".

The diurethane accumulating as distillation residue in a purity of around 99% after removal of the low- and medium-boiling fractions by distillation may be subjected to thermal urethane cleavage by known methods. There is no need for additional complicated and cost-intensive purification steps such as, for example, complete distillation of the diurethane. The urea derivative corresponding to the formula in the preceding paragraph, which is present in trace amount (up to 1%), may be recycled for reuse in the process of the present invention after it has been removed from the thermal urethane cleavage stage.

The process according to the invention may of course also be carried out continuously, for example in cascades of suitable stirred reactors.

In all embodiments of the present invention, there is no need to use a catalyst or an inert gas to drive out the ammonia.

Having thus described our invention, the following Example is given as being illustrative thereof. In the following Example, all percentages are by weight.

EXAMPLE

The reactor used was a 2 liter stirred autoclave with jacket heating surmounted by a packed column (length: 50 cm, diameter: 3 cm, packing: 4×4 mm VA steel wire mesh rings), a coil condenser, a pressure-holding valve at the head of the condenser, condenser and pressure-holding valve heatable and thermostatically temperature-controlled. 191 g (3.18 mol) of urea in 452 g (6.1 mol) of n-butanol were introduced into the reactor and heated with stirring to 220° C. at a condenser temperature adjusted to 70° C. The pressure-holding valve was adjusted so that ammonia escaped while the butanol boiled under reflux. Up to equilibrium adjustment after about 1 hour, 55% of the theoretically expected quantity of ammonia was removed. A solution of 168 g (1.45 mol) of 1,6-diaminohexane (HDA) in 200 g (2.7 mol) of n-butanol was then added over a period of 2 hours, after which the mixture was stirred at 220° C. The release of ammonia abated after 1 hour. The reaction mixture was then stirred for another 8 hours until virtually no more ammonia escaped. The reaction mixture was then worked up by distillation.

To work up the reaction mixture by distillation, n-butanol was first largely distilled off in vacuo (15 mbar, oil bath temperature 90° C.). 462 g of residue containing 95.0% of hexamethylene dibutyl urethane were left, corresponding to a yield, based on the diaminohexane used, of 95.9% (supercritical fluid chromatography, internal standard). 2.3% of carbamic acid butyl ester, 1.3% of dibutyl carbonate, 0.1% of N-butyl carbamic acid butyl ester and 1.1% of butanol were determined as secondary components by gas chromatography (internal standard). The sum of these components was 99.8%. No oligoureas or polyureas were detected.

The volatile components mentioned (medium-boiling components) were completely removed in vacuo at 140° C./ 0.05 mbar. The hexamethylene dibutyl urethane thus obtained had a purity of 99%. The diurethane was readily cleaved in this form by a known method. Such methods are described, for example, in EP-A-0 061 013, EP-A-0 092 738 or EP-A-0 542 106.

A urea derivative having the following structure was obtained as the only secondary product:

BuOCONH—(CH$_2$)$_6$—NHCONH—(CH$_2$)$_6$—NHCOOBu.

This product was isolated by preparative gel permeation chromatography and identified by NMR spectroscopy. No oligoureas or polyureas were detected.

The secondary product (urea derivative) may be removed by high vacuum distillation and recycled under the reaction conditions described above after the addition of urea and butanol to maintain the above-mentioned stoichiometric ratio for HDA:urea:butanol.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a diurethane corresponding to the formula

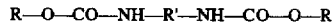

R—O—CO—NH—R'—NH—CO—O—R    (I)

in which

R represents a residue obtained by removal of a hydroxyl group from a monohydric alcohol having a boiling point below 180° C. and R' represents a difunctional (cyclo)aliphatic hydrocarbon radical containing from 2 to 18 carbon atoms, provided that at least two carbon atoms are present between the two nitrogen atoms comprising a) reacting a urea with an alcohol corresponding to the formula ROH in amounts such that the molar ratio of alcohol to urea is at least 1:1 at a temperature of from about 150 to about 300° C., b) removing at least 10 mol %, based on the molar quantity of urea used in a), of ammonia generated during a), c) introducing a diamine represented by the formula H$_2$N—R'—NH$_2$ into the reaction mixture remaining from b), d) reacting the mixture of c) at a temperature of from about 150° to about 300° C., and e) distilling the mixture remaining after d) to remove volatile substituents.

2. The process of claim 1 in which the diamine corresponding to the formula H$_2$N—R'—NH$_2$ is selected from hexane-1,6-diamine, 3-amino-methyl-3,5,5 -trimethyl cyclohexylamine and bis-(4aminocyclohexyl)-methane.

3. The process of claim 2 in which the alcohol corresponding to the formula ROH is n-butanol.

4. The process of claim 1 in which the alcohol corresponding to the formula ROH is n-butanol.

5. The process of claim 1 in which R' represents a difunctional (cyclo)aliphatic hydrocarbon radical containing from 4 to 15 carbon atoms.

6. The process of claim 1 in which the diamine added in step c) is in the form of a solution in which at least 5 wt % of the solution is the diamine which solution has been formed with additional alcohol corresponding to the formula ROH.

* * * * *